United States Patent [19]

Kuroda

[11] Patent Number: 4,981,803
[45] Date of Patent: Jan. 1, 1991

[54] REAGENT FOR RETICULOCYTE COUNTING BY FLOW CYTOMETRY

[75] Inventor: Tomoyuki Kuroda, Kakogawa, Japan

[73] Assignee: Toa Medical Electronics Co., Ltd., Kobe, Japan

[21] Appl. No.: 117,026

[22] Filed: Nov. 4, 1987

[30] Foreign Application Priority Data

Jul. 31, 1987 [JP] Japan .................................. 62-192413

[51] Int. Cl.$^5$ ...................... C12Q 1/00; G01N 33/48; G01N 33/533; G01N 33/554
[52] U.S. Cl. ............................................. 436/63; 435/2; 435/4; 435/35; 436/56; 436/172; 436/519; 436/520; 436/546
[58] Field of Search ................. 436/63, 172, 519, 520, 436/56, 546; 435/4, 7, 2, 35, 34; 106/22, 23

[56] References Cited

U.S. PATENT DOCUMENTS

| | | | |
|---|---|---|---|
| 4,288,543 | 9/1981 | Sielaff et al. | 435/34 |
| 4,835,101 | 5/1989 | Kao et al. | 436/172 |
| 4,835,103 | 5/1989 | Cercek et al. | 436/63 |
| 4,842,646 | 6/1989 | Gamblin | 106/20 |

FOREIGN PATENT DOCUMENTS 0034058 of 1987 Japan .

OTHER PUBLICATIONS

Walter C. Holmes and J. Ferris Darling, "The Hydrolysis of Auramine", Journal of the American Chemical Society, 46, 2343–2348 (1924).

Primary Examiner—Robert J. Warden
Assistant Examiner—Kimberly A. Trautman
Attorney, Agent, or Firm—Fitch, Even, Tabin & Flannery

[57] ABSTRACT

A reagent for reticulocyte counting by flow cytometry which comprises two solutions, namely, a stock solution for staining in which a dye is dissolved in a nonaqueous solvent, and a buffer solution which satisfies the optimum staining conditions.

By combining these two solutions immediately before measurement, a stable final staining solution for reticulocyte counting can always be obtained.

2 Claims, 5 Drawing Sheets

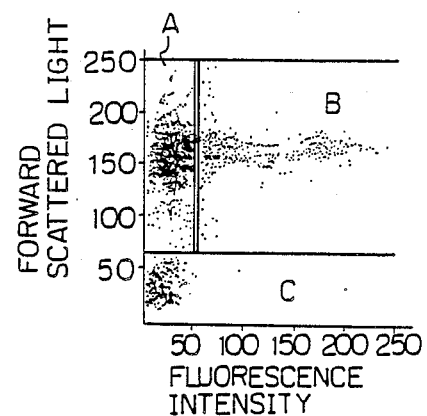
Fig. 3-I-a
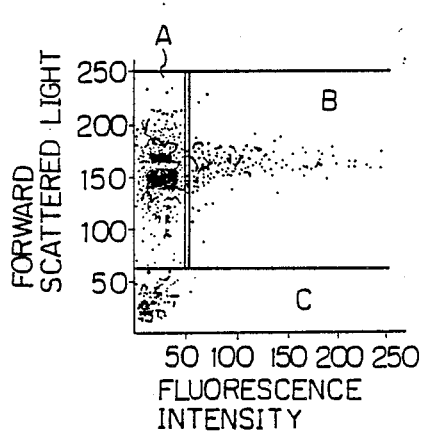
Fig. 3-I-b
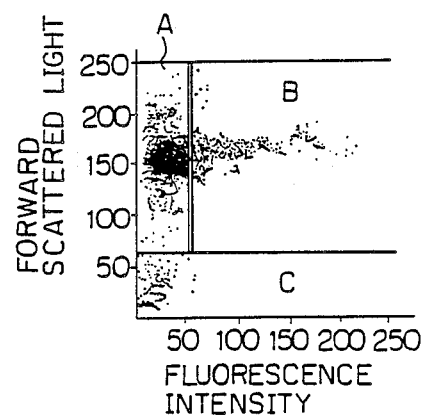
Fig. 3-I-c

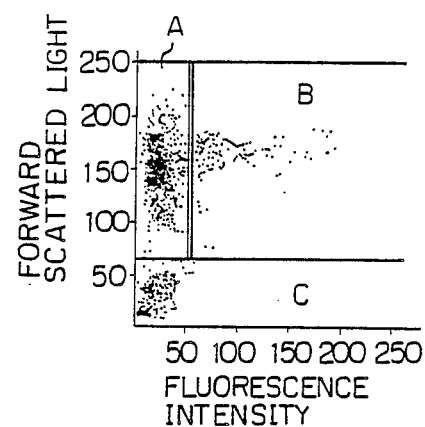
Fig.3-II-a
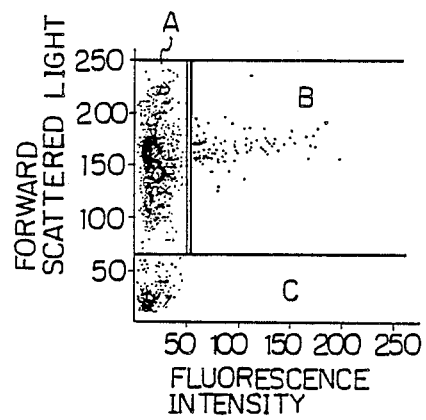
Fig.3-II-b
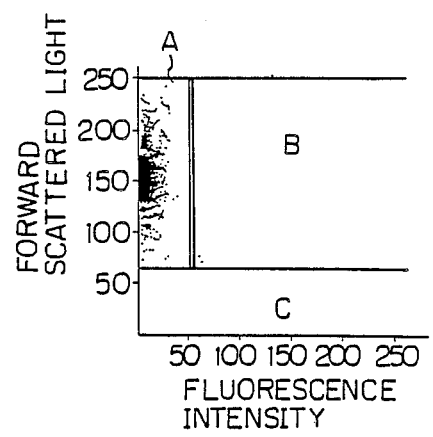
Fig.3-II-c

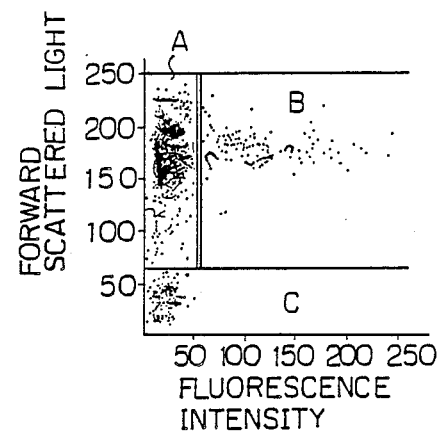
Fig.3-III-a
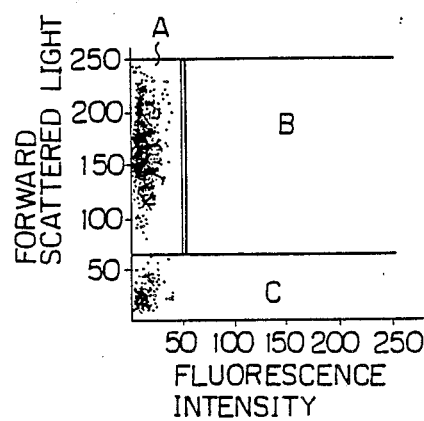
Fig.3-III-b
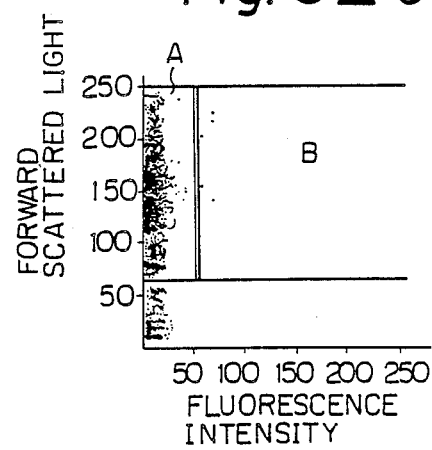
Fig.3-III-c

REAGENT FOR RETICULOCYTE COUNTING BY FLOW CYTOMETRY

The present invention relates to a reagent for reticulocyte counting by flow cytometry. More particularly, the present invention relates to a reagent for reticulocyte counting by flow cytometry which consists of two solutions, namely, a stock solution for staining and a buffer solution.

Immature erythrocytes in the blood are called reticulocytes, and normally account for 0.7-2.2% of the total count of erythrocytes. Determination of reticulocyte count helps confirmation of the diagnosis of such diseases as acute internal hemorrhage, hemolytic anemia, aplastic anemia, etc., and also helps in monitoring the progress of a patient's conditions after drug administration; thus it is regarded as being very important in the field of laboratory tests.

A method which has been employed for the counting of said reticulocytes is conducted as follows: a smear of blood sample stained with a basic dye such as new methylene blue, brilliant cresyl blue, etc. is observed and the percentage of the count of stained reticulocytes is determined with respect to the total erythrocyte count.

This method requires a lot of time and involves a considerable workload for pre-treatment of blood samples, e.g. staining, etc., as well as for visual counting after staining, and is inappropriate when the number of samples is large.

Therefore, many methods have been proposed in which reticulocyte counting is automated by the application of flow cytometry. For example, methods in which a fluorochrome reagent containing Auramine O is used for counting reticulocytes by flow cytometry are disclosed in Japanese Patent Public Disclosure No. 280565/1986 and Japanese Patent Public Disclosure No. 34058/1987.

W. C. Holmes, et al. explain that the above-mentioned Auramine O undergoes a hydrolysis reaction, as shown below, which is catalyzed by an acid or an alkali, and that the higher the reaction temperature, the larger the rate constant (Journal of The American Chemical Society, 46, 2343-2348, (1924)).

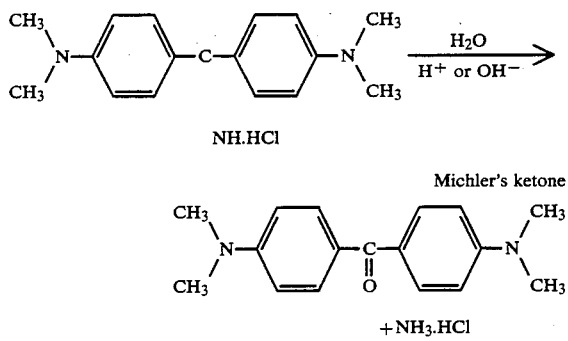

The time required for 5% of Auramine O to be hydrolyzed under the conditions specified in the aforementioned article, calculated on the basis of data described in the same, is shown in Table 1. In the Table, K denotes the rate constant.

TABLE 1

| Time Required for 5% of Auramine O to be Hydrolyzed | | | |
|---|---|---|---|
| pH | Temperature (°C.) | K*1 (/sec) | Time required for 5% to be hydrolyzed*2 (hr) |
| c.a. 7 | 30 | $2.1 \times 10^{-7}$ | 67.8 |
| " | 40 | $6.4 \times 10^{-7}$ | 22.3 |
| " | 45 | $1.4 \times 10^{-6}$ | 10.0 |
| " | 50 | $2.6 \times 10^{-6}$ | 5.57 |
| " | 60 | $6.4 \times 10^{-6}$ | 2.22 |
| " | 70 | $1.5 \times 10^{-5}$ | 0.923 |
| " | 80 | $3.5 \times 10^{-5}$ | 0.427 |
| " | 90 | $7.6 \times 10^{-5}$ | 0.187 |
| " | 100 | $1.6 \times 10^{-4}$ | 0.0896 |
| 3.5 | " | $1.8 \times 10^{-4}$ | 0.0810 |
| 3.0 | " | $2.0 \times 10^{-4}$ | 0.0720 |
| 2.9 | " | $2.5 \times 10^{-4}$ | 0.0577 |
| 2.2 | " | $8.8 \times 10^{-4}$ | 0.0162 |
| 1.8 | " | $3.8 \times 10^{-3}$ | 0.00372 |

*1 Converted from literature values ($hr^{-1}$)
*2 Theoretical values

Since, however, Table 1 cannot cover all of the conditions under which Auramine O is used for counting reticulocytes, Experiment 1 was conducted to determine in detail the time required for 5% of Auramine O to be hydrolyzed under acutal staining conditions. This experiment is described below.

Experiment 1

Staining solutions with the four different compositions shown in Table 2 were prepared and stored in baths whose temperatures were controlled at 5.4° C., 22.3° C. and 39.0° C., respectively, and the residual amount of Auramine O in each solution was studied up to the 12th day by HPLC.

TABLE 2

| Composition of Staining Solution* | | |
|---|---|---|
| Sample No. | pH | Auramine O Concentration (μg/ml) |
| 1 | 7.0 | 1,000 |
| 2 | 7.5 | 750 |
| 3 | 8.0 | 500 |
| 4 | 8.5 | 250 |

*(N-2-hydroxyethylpiperazine-N'-2-ethane sulfonic acid)

FIG. 1 shows an example of results at 39° C. From this figure, it will be clearly seen that the hydrolysis reaction of Auramine O is of first-order. The hydrolysis reaction rate constants of each staining solution at respective temperatures are shown in Table 3.

TABLE 3

| | Hydrolysis Rate of Auramine O at each pH and Temperature ($sec^{-1}$) | | |
|---|---|---|---|
| Sample No. | pH | 5.4° C. | 22.3° C. | 39.0° C. |
| 1 | 7.0 | — | $1.64 \times 10^{-7}$ | $7.93 \times 10^{-7}$ |
| 2 | 7.5 | $2.91 \times 10^{-8}$ | $2.18 \times 10^{-7}$ | $1.65 \times 10^{-6}$ |
| 3 | 8.0 | $5.52 \times 10^{-8}$ | $5.81 \times 10^{-7}$ | $3.50 \times 10^{-6}$ |
| 4 | 8.5 | $1.69 \times 10^{-7}$ | $1.58 \times 10^{-6}$ | $8.97 \times 10^{-6}$ |

The relationship between the hydrolysis rate and temperature for each staining solution (Arrhenius plot) is shown in FIG. 2. As shown in the figure, the points of measurement form an almost straight line. Thus, hydrolysis rate constants at temperatures not actually employed in the experiment can be obtained easily. From the experimental results described above, the time required for 5% of Auramine O to be hydrolyzed under conditions actually employed for staining reticulocytes was estimated as shown in Table 4.

TABLE 4

| | Estimated Time Required for 5% Auramine O to be Hydrolyzed under Conditions of Auramine O Staining (hr) | | | | | | | |
|---|---|---|---|---|---|---|---|---|
| | Temp. (°C.) | | | | | | | |
| pH | 5 | 10 | 15 | 20 | 25 | 30 | 35 | 40 |
| 7.0 | 536.65 | 309.20 | 181.62 | 108.60 | 66.02 | 40.91 | 25.69 | 16.40 |
| 7.5 | 537.87 | 277.20 | 146.13 | 78.85 | 43.32 | 24.31 | 13.89 | 8.086 |
| 8.0 | 260.48 | 131.44 | 68.04 | 35.95 | 19.40 | 10.71 | 6.009 | 3.442 |
| 8.5 | 85.47 | 44.44 | 23.64 | 12.85 | 7.124 | 4.034 | 2.321 | 1.361 |

A staining solution whose residual dye amount had been determined by HPLC was filtered for the purpose of avoiding possible adverse effects by employing precipitated Michler's ketone. To 2 ml of the filtrate, 10 μl of EDTA anti-coagulated fresh blood was added. After incubation for 1 minute, the sample was subjected to flow cytometer in which argon ion laser of 488 nm (10 mW) was used as a light source, and forward scattering and fluorescence from blood corpuscles were determined.

The HPLC results are shown in Table 5 for the staining solution (pH 8.5) shown in Table 2. Samples stored at three levels of temperature (5.4° C., 22.3° C. and 39.0° C.) were subjected to measurement five times during the period between the day of preparation and the 12th day; that is, 60 measurements were made altogether. In Table 5, however, the results at pH 8.5 only are shown because at this pH, the effects of temperature at which the staining solution was stored are maximum.

As shown in FIG. 3-I-a to FIG. 3-III-c, the intensity of staining measured by flow cytometry decreases with the decrease in the residual amount of dye determined by HPLC.

TABLE 5

| | Residual Amount of Dye (%) | | |
|---|---|---|---|
| | Time after preparation | | |
| Temperature | 2 hrs. | 2 days | 12 days |
| 5.4° C. | 99.9 | 97.3 | 83.9 |
| 22.3° C. | " | 74.7 | 24.1 |
| 39.0° C. | " | 21.2 | 0.9 |

As shown above, the results of Experiment 1 revealed that Auramine O is hydrolyzed even under normal staining conditions claimed in Japanese Patent Public Disclosure No. 280565/1986. The solubility in water of the Michler's ketone which is formed at the time of hydrolysis is extremely small. It is only dissolved in an amount equivalent to not more than 10 μg/ml of Auramine O. For example, in a staining solution whose pH is 8.0 and Auramine O concentration 400 μg/ml, the Michler's ketone precipitates in 5 days when stored at a temperature of 4° C., and in about half a day when stored at room temperature. Therefore, if this staining solution is used, reticulocyte counting will be adversely affected.

One method of solving this problem would be to solubilize the Michler's ketone by the addition of a solvent. However, this method is directed only at reducing the interference caused by the precipitation of Michler's ketone with reticulocyte counting, and does not compensate for the deterioration of the reagent's characteristic due to the decrease in Auramine O content.

BRIEF DESCRIPTION OF THE DRAWINGS

FIGS. 3-I-a, 3-I-b, 3-I-c, b 3-II-a, 3-II-b, 3-II-c, 3-III-a, 3-III-b and 3-III-c show the results of measurements of forward scattered light and fluorescence from blood corpuscles when a staining solution at pH 8.5 was used under the time and temperature conditions shown in Table 5, respectively. Here, the configuration of these figures corresponds to the entry in Table 5.

Figure 1:
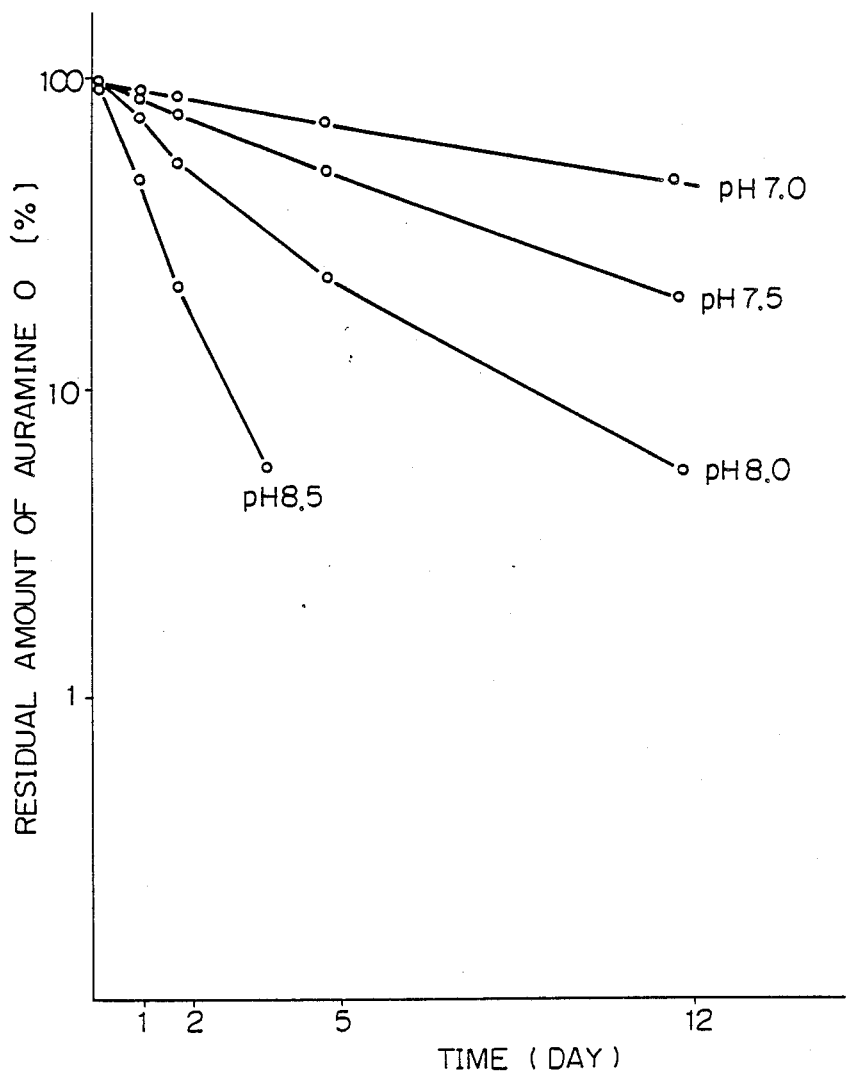
FIG. 1 shows the change with time of the residual Auramine O amount up to the 12th day after staining solutions of four compositions shown in Table 2 were prepared and stored in a airbath maintained to 39.0° C.
Figure 2:
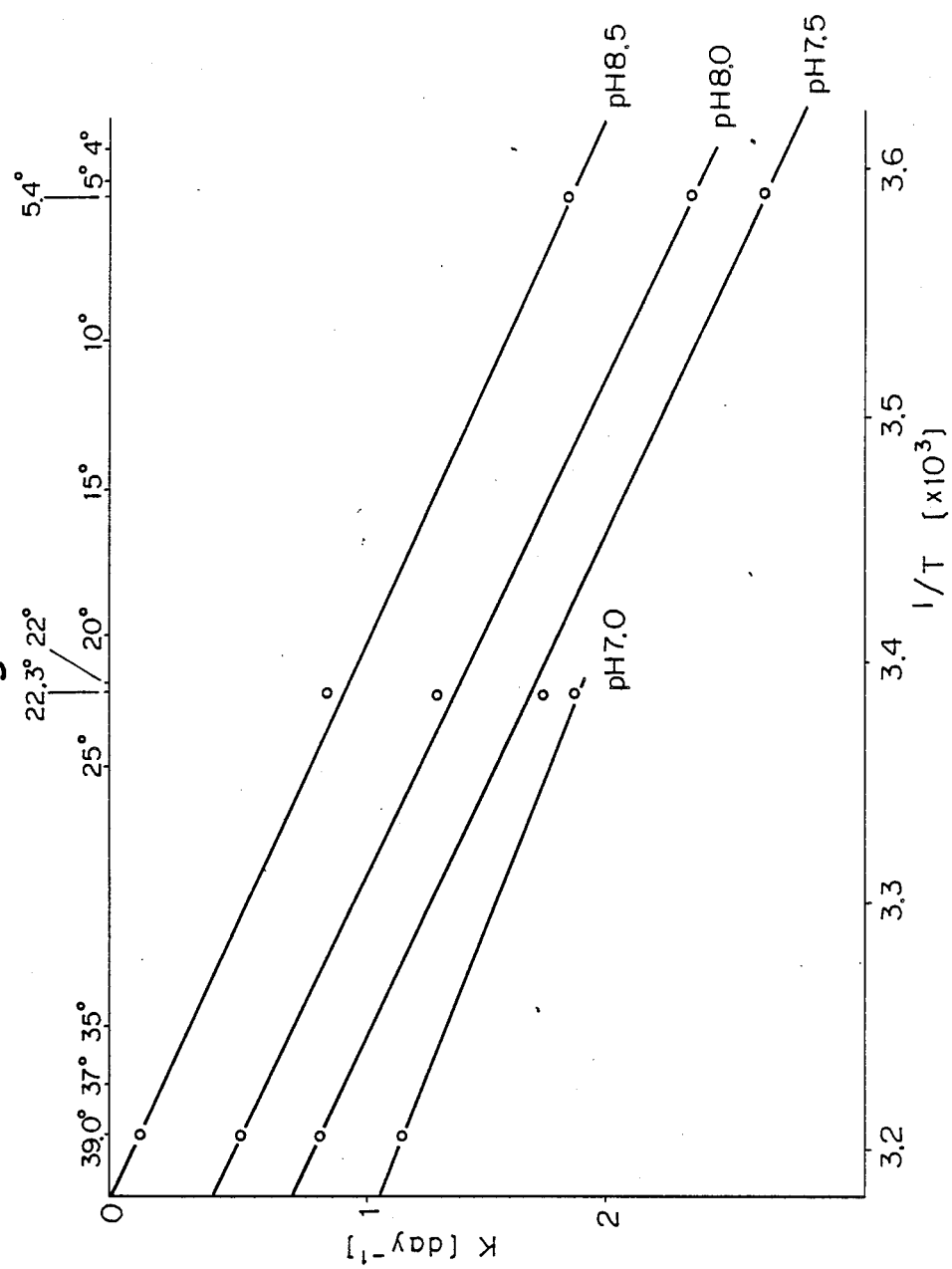
FIG. 2 is an Arrhenius plot which shows the relationship between the hydrolysis rate and temperature for each of the aforementioned staining solutions.

In the above figures, A shows the range corresponding to mature erythrocytes, B: reticulocytes and C: platelets, respectively.

DETAILED DESCRIPTION OF THE INVENTION

The present invention provides a stable reagent for reticulocyte counting which is free from deterioration, i.e., decrease in the dye content, wherein for the purpose of preventing the decrease in the amount of a fluorochrome, Auramine O due to hydrolysis, the reagent is divided into two solutions, namely, a dye solution in which the fluorochrome is dissolved in an anhydrous solvent, and an aqueous buffer solution which satisfies the optimum staining conditions; and these two solutions are mixed immediately prior to use.

In other words, the present invention provides a reagent for flow cytometry which consists of two solutions, a stock solution for staining in which a dye is dissolved in a non-aqueous solvent, and a buffer solution which satisfies the optimum staining conditions.

The stock solution for staining comprises Auramine O and a nonaqueous solvent, and the nonaqueous solvent should satisfy the following requirements:

(1) It should be polar enough to dissolve Auramine O, and the solubility of Auramine O in it should not be less than several %.
(2) It should not interfere with the blood corpuscles. At least, it should not deform the results of counting by flow cytometry.
(3) It should not adversely affect the flow system of the apparatus for flow cytometry.
(4) It should have little volatility, and hardly any propensity to deteriorate, degenerate, or decrease over long periods of storage.

In view of these requirements, alcohols comprise preferable solvents, and ten alcoholic solvents were examined in detail taking account of these conditions.

First, the effects of the solvent addition on the reticulocyte counting mentioned under item (2) above was examined in the following Experiment 2. In actual flow cytometric analysis, Auramine O is dissolved in a solvent, and this Auramine O stock solution and a buffer solution are mixed to prepare a final staining solution for reticulocyte counting. In this experiment, however, a solvent alone was added to a staining solution which already contained Auramine O, and the effects of the solvent addition on the reticulocyte count determination were examined.

| Experiment 2 | |
|---|---|
| Auramine O | 400 mg/l |
| Phosphoric acid | 20 mM/l |
| Sodium chloride | 150 mM/l |

Staining solutions of pH 8.0 with the composition shown above were prepared immediately prior to measurement so as to contain various solvents at concentrations of 0.40%, 0.63%, 1.00%, 1.6%, 2.5%, 4.0%, 6.25%, 10.0%, 16.0% and 25.0%, respectively (all percentages are expressed by volume).

To 2 ml of each staining solution, 10 μl of EDTA anti-coagulated fresh blood was added. The blood corpuscles were stained for 30 seconds at 25° C., and the forward scattering and fluorescence were measured by flow cytometry.

The concentration with which erytrocytolysis occurs differs with the type of solvent. In the case of solvents which cause erythrocytolysis even when the solvent content in the staining solution is over 10%, little or no effects were observed on measurements of forward scattered light up to a solvent content of about 10%; in the case of solvents which cause erythrocytolysis at a solvent content of less than about 10%, the same was true until immediately prior to the occurrence of the cytolysis phenomena.

On the other hand, the intensity of fluorochrome staining decreases with the increase in the amount of solvent added. For such cases the reticulocyte counting is free from suffering the effects of solvent addition up to a certain critical amount by increasing the sensitivity of the flow cytometry. The critical amount of addition differs with the type of solvent.

In relation to the addition of various solvents, the content of solvent over which erythrocytolysis occurs and the maximum possible solvent content that allows the reticulocyte counting by flow cytometry are shown in Table 6.

TABLE 6

Solvent Content which Allows Reticulocyte Counting by Flow Cytometer (v/v %)

| Solvent | Content over which erythrocytolysis occurs | Maximum possible content which allows reticulocyte counting by flow cytometry |
|---|---|---|
| methanol | more than 25 | 6.25 |
| ethanol | more than 25 | 6.25 |
| n-propanol | 16.0 | 2.5 |
| ethylene glycol | more than 25 | 6.25 |
| diethylene glycol | more than 25 | 2.5 |
| triethylene glycol | 4.0 | 1.6 |
| ethylene glycol monomethyl ether | 16.0 | 4.0 |
| ethylene glycol monoethyl ether | 10.0 | 2.5 |
| ethylene glycol mono-(n-butyl) ether | 6.25 | 2.5 |
| diethylene glycol monoethyl ether | 16.0 | 2.5 |

From Table 6, it is obvious that the maximum amount of solvent that can be added is determined by the range in which flow cytometry is possible. However, since it is desirable that the decrease in the intensity of fluorescence be minimized, it is preferable that the amount of solvent to be added is also minimized.

In order for reticulocyte counting to be possible, the final staining solution should have a desired dye concentration. For that purpose, a desired amount of dye should be dissolved in a stock solution for staining. On the other hand, as is explained above, the amount of solvents contained in the stock solution for staining should be as small as possible in the final staining solution. Therefore, a solvent in which Auramine O has a large solubility is preferred. If such a solvent is selected, a desired concentration of the final staining solution can be obtained with the addition of a smaller amount of a stock solution for staining (and therefore, a smaller amount of solvent). This corresponds to item (1) mentioned above as a requirement for a suitable nonaqueous solvent.

Of course, a solvent in which Auramine O has such small solubility that a desired concentration in the final staining solution cannot be obtained unless the solvent is added in an amount exceeding the maximum allowable amount shown in Table 6 cannot be used for a stock solution for staining.

For example, the preparation of a staining solution with the final dye concentration shown in Table 2 requires the solubility of Auramine O in the solvent to be as shown in Table 7 for each level of solvent content in the final staining solution. Table 7 may be interpreted as follows: in order to have the dye concentration of 1,000 μg/ml in the final staining solution at a solvent content level of 1 v/v %, the solubility of Auramine O in the solvent should be 10.0 g/100 ml.

The actual solubility in each solvent is 2–3 g/100 ml in the cases of methanol, ethanol and n-propanol. The maximum amount of ethanol and methanol that can be added is 6.25 v/v %, as shown in Table 6, and in order to have the dye concentration of 1,000 μg/ml in the final staining solution, a solubility of 1.6 g/100 ml is required, as shown in Table 7. Methanol and ethanol can therefore be used from the viewpoint of solubility. On the other hand, the maximum amount of n-propanol that can be added is 2.5 v/v %. Table 7 shows that this degree of solubility is too small to provide a dye concentration of 1,000 μg/ml in the final staining solution, as the maximum dye concentration in the final staining solution could at most be between 500 and 750 μg/ml.

TABLE 7

Solubility Necessary for Preparing Final Staining Solution (g/100 ml)

| Content of solvent (v/v %) | Dye concentration in the final staining solution (mg/l or μg/ml) | | | |
|---|---|---|---|---|
| | 250 | 500 | 750 | 1,000 |
| 1.0 | 2.5 | 5.0 | 7.5 | 10.0 |
| 1.6 | 1.6 | 3.2 | 4.8 | 6.4 |
| 2.5 | 1.0 | 2.0 | 3.0 | 4.0 |
| 4.0 | 0.63 | 1.25 | 1.88 | 2.5 |
| 6.25 | 0.4 | 0.8 | 1.2 | 1.6 |

In the cases of ethylene glycol, diethylene glycol and triethylene glycol, the solubility of Auramine O in these solvents is 6–8%; therefore, the staining solution of the dye concentrations shown in Table 2 can easily be prepared within the range of the maximum possible amount of solvent addition shown in Table 6.

Of the solvents listed in Table 1, the Auramine O solubility in the remaining 4 solvents is 2-3% which is too small to prepare a staining solution of 1,000 μg/ml without interfering with the reticulocyte counting, and the maximum concentration of the dye in the staining solution that can be prepared with this solvent is 750 μg/ml. In addition, these four solvents are not appropriate from the viewpoint of item (3) above.

In regard to item (4), methanol, ethanol and n-propanol have high volatility, and thus and not appropriate.

Therefore, the solvents which can be used for the objects of the present invention are preferably ethylene glycol, diethylene glycol and triethylene glycol; if such characteristics as the effects on erythrocytes and viscosity are further considered, ethylene glycol is the most preferable.

A buffer solution contains a buffering agent and an osmotic pressure-compensating agent. A buffering agent is added to maintain the pH of a staining solution, and an acceptable content is one wherein fluorescent intensity change does not occur with the pH fluctuation of the staining solution. An osmotic pressure-compensating agent is added to prevent extreme deformation of blood corpuscles.

The contents of these agents are as described in Japanese Patent Public Disclosure No. 280565/1986; the final staining solution is prepared so that the concentration of an osmotic pressure-compensating agent is 5-20 mg/ml, and the pH is adjusted to 6.0-9.5.

The reagent for the present invention comprises two solutions, namely, a stack solution for staining and a buffer solution. In this reagent, the dye Auramine O is maintained in a nonaqueous solvent until immediately before measurement, so that Michler's ketone which affects the reticulocyte counting adversely will not be precipitated, and any decrease in the amount of Auramine O during storage can also be prevented. By combining these two solutions immediately before measurement, a stable final staining solution for reticulocyte counting can always be obtained.

In the following, the present invention is further illustrated in detail by example.

EXAMPLE

First, Solution 1 and Solution 2 whose compositions are as shown below were prepared:

| Ingredient | Concentration |
|---|---|
| Solution 1 | |
| HEPES | 20 mM |
| NaCl | 160 mM |
| | pH 8.5 |
| Solution 2 | |
| Auramine O | 1.25 w/v % |
| ethylene glycol | the rest |

Two ml of a staining solution was prepared by mixing 1960 μl of Solution 1 and 40 μl of Solution 2 so that the Auramine O concentration became 250 μg/ml. To this solution, 10 μl of EDTA anti-coagulated fresh blood was added to prepare a sample. After staining had been conducted for 30 seconds at room temperatures, the sample was subjected to the aforementioned flow cytometer to measure the forward scattered light and fluorescence.

As described above, the two-solution composition of the present invention allows measurement immediately after the staining solution is made. Therefore, decrease in the residual amount of dye with the lapse of time after the preparation of a staining solution, as observed in the aforementioned Table 5 of Experiment 2 and FIG. 3-II-a to FIG. 3-III-c, is not observed at all. In other words, by combining Solution 1 and Solution 2 immediately before use, results that are the same as those shown in Table 5 (the column corresponding to "2 hours after the preparation of staining solution"), FIG. 3-I-a, FIG. 3-I-b and FIG. 3-I-c can always be obtained.

What is claimed is:

1. A kit for preparing a reagent for reticulocyte counting by flow cytometry which kit comprises a first, nonaqueous, solution and a second, aqueous, solution, said first solution comprising a nonaqueous solvent selected from the group consisting of ethylene glycol, triethylene glycol, and diethylene glycol, and a fluorescent diphenylmethane dye capable of dyeing a reticulocyte; and said second solution being an aqueous buffer solution suitable for staining reticulocytes.

2. A reagent according to claim 1 in which the buffer solution is a member of the group consisting of HEPES buffer solution, phosphate buffer solution or Tris-Tricine buffer solution.

* * * * *

UNITED STATES PATENT AND TRADEMARK OFFICE
CERTIFICATE OF CORRECTION

PATENT NO. : 4,981,803

DATED : January 1, 1991

INVENTOR(S) : Tomoyuki Kuroda

It is certified that error appears in the above-identified patent and that said Letters Patent is hereby corrected as shown below:

ON THE TITLE PAGE

[73] Assignee, change "Toa" to --TOA--.

Column 1, line 55, change "NH.HCl" to --NH·HCl--.
Column 1, line 62, change "$NH_3$.HCl" to --$NH_3$·HCl--.
Column 2, line 24, change "acutal" to --actual--.
Column 2, line 43, after "*" insert --20 mM HPEES--.
Column 2, line 43, after "acid)" insert --buffer solution, 160 mM-(NaCl)--.
Column 3, line 13, change ".of" to --of--.
Column 3, lines 14-15, change "To 2 ml of the filtrate, 10 $\mu$l of EDTA anticoagulated fresh blood was added." to --Ten $\mu$l of EDTA anticoagulated fresh blood was added to 2 ml of the filtrate.--.
Column 4, line 34, after "O" insert a comma.

UNITED STATES PATENT AND TRADEMARK OFFICE
CERTIFICATE OF CORRECTION

PATENT NO. : 4,981,803
DATED : January 1, 1991
INVENTOR(S) : Tomoyuki Kuroda

It is certified that error appears in the above-identified patent and that said Letters Patent is hereby corrected as shown below:

Column 5, line 23, change "erytrocytolysis" to --erythrocytolysis--.

Column 6, line 64, delete "5".

Signed and Sealed this

Eighteenth Day of February, 1992

Attest:

HARRY F. MANBECK, JR.

*Attesting Officer*    *Commissioner of Patents and Trademarks*